United States Patent [19]

Regel et al.

[11] Patent Number: 4,910,213
[45] Date of Patent: * Mar. 20, 1990

[54] ANTIMYCOTIC AGENTS

[75] Inventors: Erik Regel, Wuppertal; Klaus Böckmann, Cologne; Karl H. Büchel, Burscheid; Manfred Plempel, Haan, all of Fed. Rep. of Germany

[73] Assignee: Bayer Aktiengesellschaft, Leverkusen, Fed. Rep. of Germany

[*] Notice: The portion of the term of this patent subsequent to Oct. 24, 2006 has been disclaimed.

[21] Appl. No.: 787,833

[22] Filed: Oct. 16, 1985

[30] Foreign Application Priority Data

Nov. 2, 1984 [DE] Fed. Rep. of Germany ....... 3440114

[51] Int. Cl.$^4$ .............................................. A61K 31/41
[52] U.S. Cl. .................................................... 514/383
[58] Field of Search ......................................... 514/383

[56] References Cited

U.S. PATENT DOCUMENTS

| | | | |
|---|---|---|---|
| 4,423,212 | 12/1983 | Skulnick | 536/29 |
| 4,547,214 | 10/1985 | Crowley et al. | 514/583 |
| 4,618,616 | 10/1986 | Richardson et al. | 514/383 |

FOREIGN PATENT DOCUMENTS

| | | |
|---|---|---|
| 0044605 | 1/1982 | European Pat. Off. . |
| 0164246 | 12/1985 | European Pat. Off. . |
| 0180850 | 5/1986 | European Pat. Off. . |
| 3307216 | 9/1984 | Fed. Rep. of Germany . |

*Primary Examiner*—Richard L. Raymond
*Attorney, Agent, or Firm*—Sprung Horn Kramer & Woods

[57] ABSTRACT

A method of combating mycoses which comprises administering to a patient in need thereof an antimycotic effective amount of an azolylcyclopropyl-azolylmethyl-carbinol derivative of the formula

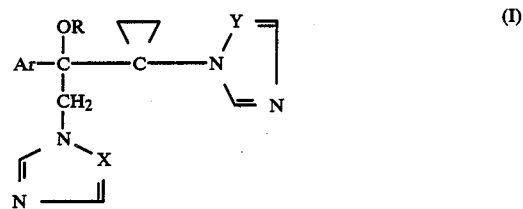

in which
Ar is optionally substituted aryl or optionally substituted heteroaryl,
R is hydrogen, alkyl, alkenyl, alkinyl, trialkylsilyl, optionally substituted phenylalkyl or the acyl radical,
X is a nitrogen atom or the CH group, and
Y is a nitrogen atom or the CH group,
or an acid addition salt thereof.

4 Claims, No Drawings

ANTIMYCOTIC AGENTS

The present invention relates to the use of new substituted azolylcyclopropyl-azolylmethyl-carbinol derivatives as antimycotic agents, in particular as antimycotics.

It has already become generally known that certain diazolyl derivatives such as, for example, 1,3-di-(1,2,4-triazol-1-yl)-2-(3-chlorophenyl)- or -(4-chlorophenyl)- or -phenyl-2-propanol have antimycotic properties (compare EP-OS (European Published Specification) 0,044,605). However, the action of these substances is not always completely satisfactory in all areas of indication.

It has been found that the new substituted azolylcyclopropyl-azolylmethyl-carbinol derivatives of the formula (I)

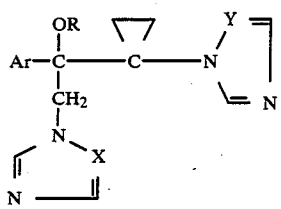

in which

Ar represents optionally substituted aryl or optionally substituted heteroaryl,

R represents hydrogen, alkyl, alkenyl, alkinyl, trialkylsilyl, optionally substituted phenylalkyl or the acyl radical, X represents a nitrogen atom or the CH group, and Y represents a nitrogen atom or the CH group, and their acid addition salts have good antimicrobial, in particular antimycotic, properties.

Surprisingly, the new substituted azolylcyclopropyl-azolylmethyl-carbinol derivatives of the formula (I) which are to be used according to the invention show a better spectrum of action in certain areas of indication than the diazolyl derivatives known in the state of the art, 1,3-di-(1,2,4-triazol-1-yl)-2-(3-chlorophenyl)- or -(4-chlorophenyl)- or -phenyl-2-propanol, which are compounds related in constitution and in respect of action.

The substituted azolylcyclopropyl-azolylmethyl-carbinol derivatives according to the invention are generally defined by formula (I). In this formula, Ar preferably represents phenyl which optionally has one or several, identical or different, substituents, the substituents which may be mentioned as being preferred being: halogen; alkyl, alkoxy and alkylthio each having 1 to 4 carbon atoms; halogenoalkyl, halogenoalkoxy and halogenoalkylthio each having 1 to 2 carbon atoms and 1 to 5 identical or different halogen atoms, such as fluorine and chlorine atoms; as well as phenyl or phenoxy each of which is optionally substituted by alkyl having 1 or 2 carbon atoms and/or halogen; and furthermore represents naphthyl and a 5- to 6-membered heteroaromatic which optionally has one or several, identical of different, substituents and nitrogen, oxygen and/or sulphur as the heteroatoms, the suitable substituents which are preferred being the abovementioned phenyl substituents;

R preferably represents hydrogen, straight-chain or branched alkyl having 1 to 4 carbon atoms, straight-chain or branched alkenyl and alkinyl each having 2 to 4 carbon atoms, trialkylsilyl having 1 to 4 carbon atoms in each alkyl moiety, alkylcarbonyl having 1 to 4 carbon atoms in the alkyl moiety, and represents phenylalkyl which optionally has one or several, identical or different, substituents, with 1 to 2 carbon atoms in the alkyl moiety, the suitable substituents which are preferred being the phenyl substituents already mentioned for Ar; and X and Y represent the meanings given in the definition of the invention.

Particularly preferred compounds of the formula (I) are those in which

Ar represents phenyl which optionally has one to three, in particular one or two, identical or different substituents, the substituents which may be mentioned being: fluorine, chlorine, methyl, isopropyl, tert.-butyl, methoxy, methylthio, trifluoromethyl, trifluoromethoxy, trifluoromethylthio, and phenyl or phenoxy each of which is optionally substituted by fluorine, chlorine and/or methyl; furthermore represents naphthyl and represents furyl, thienyl, pyridinyl or pyrimidinyl, each of which optionally has one or two, identical or different, substituents, suitable substituents being the abovementioned phenyl substituents;

$R^1$ represents hydrogen, methyl, ethyl, n-propyl, isopropyl, n-butyl, isobutyl, allyl, propargyl, trimethylsilyl, methylcarbonyl, ethylcarbonyl, n-propylcarbonyl, isopropylcarbonyl, n-butylcarbonyl, isobutylcarbonyl, and represents benzyl which optionally has one to three, in particular one or two, identical or different substituents, suitable substituents which are preferred being the phenyl substituents already mentioned for Ar; and X and Y represent the meanings given in the definition of the invention.

Preferred compounds according to the invention are also addition products of acids and those substituted azolylcyclopropyl-azolylmethyl-carbinol derivatives of the formula (I) in which Ar, R, X and Y have the meanings which have already been mentioned as preferred for these radicals.

The acids which can be added on preferably include hydrohalic acids such as, for example, hydrochloric acid and hydrobromic acid, in particular hydrochloric acid, also phosphoric acid, nitric acid, sulphuric acid, monofunctional and bifunctional carboxylic acids and hydroxycarboxylic acids such as, for example, acetic acid, maleic acid, succinic acid, fumaric acid, tartaric acid, citric acid, salicylic acid, sorbic acid and lactic acid, as well as sulphonic acids such as, for example, p-toluenesulphonic acid and 1,5-naphthalenedisulphonic acid.

Apart from the compounds mentioned in the preparation examples, the following compounds of the formula (Ia) may be specifically mentioned:

| Ar | X | Y |
|---|---|---|
| 4-F-C6H4 | N | CH |
| biphenyl | N | CH |
| 4-(CH3)2CH-C6H4 | N | CH |
| 4-CH3-C6H4 | N | CH |
| 4-Br-C6H4 | N | CH |
| 4-CH3O-C6H4 | N | CH |
| 2,4-Cl2-C6H3 | N | CH |
| 3,4-Cl2-C6H3 | N | CH |
| 2-thienyl | N | CH |
| 2-furyl | N | CH |
| 4-F-C6H4 | CH | N |
| biphenyl | CH | N |
| 4-(CH3)2CH-C6H4 | CH | N |
| 4-CH3-C6H4 | CH | N |
| 4-Br-C6H4 | CH | N |
| 4-CH3O-C6H4 | CH | N |
| 2,4-Cl2-C6H3 | CH | N |
| 3,4-Cl2-C6H3 | CH | N |
| 2-thienyl | CH | N |
| 2-furyl | CH | N |
| 4-Cl-C6H4 | CH | N |
| 4-F-C6H4 | CH | CH |

-continued

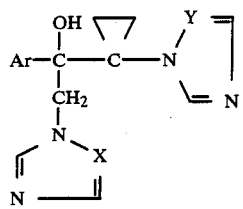

(Ia)

| Ar | X | Y |
|---|---|---|
| biphenyl | CH | CH |
| (CH₃)₂CH-phenyl | CH | CH |
| CH₃-phenyl | CH | CH |
| Br-phenyl | CH | CH |
| CH₃O-phenyl | CH | CH |
| 2,3-dichlorophenyl | CH | CH |
| 3,4-dichlorophenyl | CH | CH |
| thienyl | CH | CH |
| furyl | CH | CH |
| Cl-phenyl | CH | CH |
| thienyl | N | N |

-continued

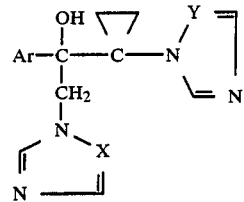

(Ia)

| Ar | X | Y |
|---|---|---|
| furyl | N | N |

The substituted azolylcyclopropyl-azolylmethyl-carbinol derivatives which are to be used according to the invention, and their acid addition salts, are described in application Ser. No. 792,089, filed Oct. 28, 1985, now pending. They can be obtained in a generally known manner by (a) in a *first step* reacting aryl azolylcyclopropyl ketones of the formula (II)

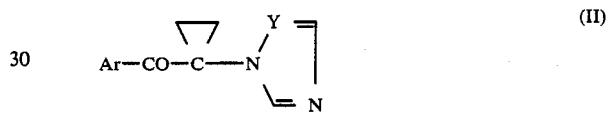

in which

Ar and Y have the abovementioned meaning, with dimethyloxosulphonium methylide of the formula (III)

$$(CH_3)_2{}^{\delta+}SO^{\delta-}-CH_2 \quad \text{(III)}$$

in the presence of a diluent such as, for example, dimethyl sulphoxide, at temperatures between 20° C. and 80° C. (in this context, compare J. Am. Chem. Soc. 87, 1363–1364 (1965)); and reacting the aryl-azolylcyclopropyloxiranes of the formula (IV) which are produced by this

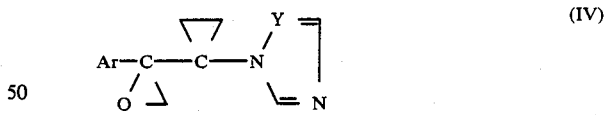

in which

Ar and Y have the abovementioned meaning, in a *second step* with azoles of the formula (V)

in which

X has the abovementioned meaning, in the presence of an inert organic solvent such as, for example, acetonitrile or dimethylformamide and in the presence of a base such as, for example, potassium carbonate or portassium hydroxide, at temperatures between 60° and 150° C.; or (b) reacting diazolyl-keto derivatives of the formula (VI)

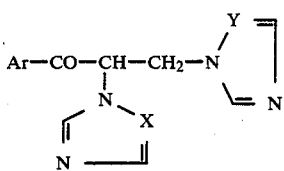 (VI)

in which

Ar, X and Y have the abovementinoed meaning, with dimethyloxosulphonium methylide of the formula (III)

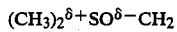 (III)

in accordance with the first step of process (a); and, where appropriate, (c) converting the hydroxy compounds of the formula (Ia) obtained by processes (a) or (b)

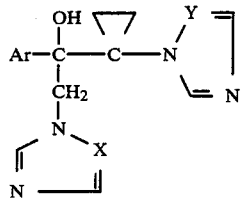 (Ia)

in which

Ar, X and Y have the abovementioned meaning, into the alcoholate in the presence of a diluent, and reacting the latter with a halide of the formula (VII)

 (VII)

in which $R^1$ represents alkyl, alkenyl, alkinyl, trialkylsilyl, optionally substituted phenylalkyl or the acyl radical, and Hal represents halogen, in the presence of an inert organic solvent such as, for example, ether or chlorinated hydrocarbons, at temperatures between 20° and 100° C.

In a preferred embodiment of the process (c), the process is advantageously started from a hydroxy compound of the formula (Ia), converting this, using an alkali metal hydride or alkali metal amide in a suitable organic solvent, into the alkali metal alcoholate, and without isolating this immediately reacting it with a halide of the formula (VII), the compounds of the formula (I), according to the invention, being obtained, with elimination of alkali metal halide, in one working step.

According to another preferred embodiment of the process (c), advantageously the preparation of the alcoholates and the alkylation are carried out in a two-phase system such as, for example, aqueous sodium hydroxide or potassium hydroxide sollution/toluene or methylene chloride, with the addition of 0.01 to 1 mole of a phase-transfer catalyst such as, for example, ammonium or phosphonium compounds, the alcoholates reacting in the organic phase or at the interface and with the halides present in the organic phase.

The acid addition salts of the compounds of the formula (I) can be obtained in a straightforward manner by customary salt-formation methods, for example by dissolution of a compound of the formula (I) in a suitable inert solvent and addition of the acid, for example hydrochloric acid, and can be isolated in a known manner, for example by filtering off, and, where appropriate, purified by washing with an inert organic solvent.

The aryl azolylcyclopropyl ketones of the formula (II) are obtained by reacting aryl halogenopropyl ketones of the formula (VIII)

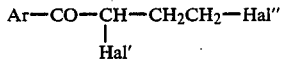 (VIII)

in which

Ar has the abovementioned meaning, and

Hal' and Hal'' represent halogen, preferably bromine or chlorine, with azoles of the formula (V)

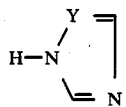 (V)

in which

Y has the abovementioned meaning, in accordance with the second step of the process (a).

The aryl halogenopropyl ketones of the formula (VIII) are known (compare, for example, DE-OS (German Published Specification) 2,521,104, DE-OS (German Published Specification) 2,320,355 and DE-OS (German Published Specification) 2,351,948); or they can be obtained in a generally customary manner.

The dimethyloxosulphonium methylide of the formula (III), which is also to be used as starting material for the first step of process (a) and for process (b) is processed in the above reactions in a freshly prepared state, by generating it in situ by reaction of trimethyloxosulphonium iodide with sodium hydride or sodium amide, in particular with potassium tert.-butylate or sodium methylate, in the presence of a diluent.

The azoles of the formula (V) which are also to be used as starting materials for the second step of process (a) are generally known compounds of organic chemistry.

The diazolyl-keto derivatives of the formula (VI) are obtained by reacting aryl azolylmethyl ketones of the formula (IX)

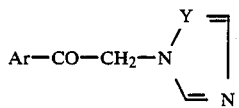 (IX)

in which

Ar and Y have the abovementioned meaning, with hydroxymethylazoles of the formula (X)

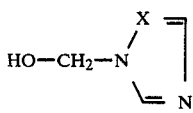 (X)

in which

X has the abovementioned meaning, in the presence of an inert organic diluent such as, for example, toluene, and in the presence of a catalyst such as, for example, piperidine acetate, preferably at the boiling point of the solvent used.

The aryl azolylmethyl ketones of the formula (IX) are known (compare, for example, DE-OS (German Published Specifications) 2,431,407, 2,610,022 and 2,638,470). The hydroxymethylazoles of the formula (X) are likewise known (compare European Pat. No. 0,006,102 and Chem. Heterocycl. Comp. 1980, 189).

The halides of the formula (VII) which are also to be used as starting materials for process (b) are generally known compounds of organic chemistry.

The compounds of the formula (I) which can be used according to the invention, and their acid addition salts, have antimicrobial, in particular potent antimycotic, actions. They have a very broad spectrum of antimycotic action, in particular on dermatophytes and yeast-like fungi as well as biphasic fungi, for example on candida species, such as Candida albicans, epidermophyton species, such as Epidermophyton floccosum, aspergillus species, such as Aspergillus niger and Aspergillus fumigatus, trichphyton species, such as Trichophyton mentagrophytes, microsporon species, such as Microsporon felineum, and torulospsis species, such as Torulospsis glabrata. This list of microorganisms does not by any means represent a limitation of the organisms which can be combated, but it merely has an illustrative nature.

Examples of indications in human medicine which may be mentioned are, for example:

Dermatomycoses and systemic mycoses caused by Trichophyton mentagrophytes and other trichophyton species, microsporon species, Epidermophyton floccosum, yeast-like fungi and biphasic fungi as well as mold fungi.

The following may be listed as examples of an area of indication in veterinary medicine:

All dermatomycoses and systemic mycoses, especially those caused by the abovementioned pathogens.

The present invention includes pharmaceutical preparations which in addition to non-toxic, inert pharmaceutically suitable excipients contain one or more active compounds according to the invention or which consist of one or more active compounds according to the invention, and processes for the production of these preparations.

The present invention also includes pharmaceutical preparations in dosage units. This means that the preparations are in the form of individual parts, for example tablets, coated tablets, capsules, pills, suppositories and ampules of which the content of active substance corresponds to a fraction or a multiple of an individual dose. The dosage units can contain, for example, 1, 2, 3 or 4 individual doses or $\frac{1}{2}$, $\frac{1}{3}$ or $\frac{1}{4}$ of an individual dose. An individual dose preferably contains the amount of active compound which is to be given in one administration and which usually corresponds to a whole, a half or a third or a quarter of a daily dose.

By non-toxic, inert pharmaceutically suitable excipients there are to be understood solid, semisolid or liquid diluents, fillers and formulation auxiliaries of all kinds.

Tablets, coated tablets, capsules, pills, granules, suppositories, solutions, suspensions and emulsions, pastes, ointments, gels, creams, lotions, powders and sprays may be mentioned as preferred pharmaceutical preparations.

Tablets, coated tablets, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatin and polyvinylpyrrolidone, (c) humectants, for example glycerol, (d) disintegrating agents, for example agar-agar, calcium carbonate and sodium bicarbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite and (i) lubricants, for example talc, calcium and magnesium stearate and solid polyethylene glycols, or mixtures of the substances listed under (a) to (i).

The tablets, coated tablets, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a microencapsulated form.

Suppositories can contain, in addition to the active compound or compounds, the customary water-soluble or water-insoluble excipients, for example polyethylene glycols, fats, for example cacao fat and higher esters (for example $C_{14}$-alcohol with $C_{16}$-fatty acid) or mixtures of these substances.

Ointments, pastes, creams and gels can contain the customary excipients in addition to the active compound or compounds, for example animal and vegetable fats, waxes, paraffins, starch, tragacanth, cellulose derivatives, polyethylene glycols, silicones, bentonites, silica, talc and zinc oxide, or mixtures of these substances.

Powders and sprays can contain the customary excipients in addition to the active compound or compounds, for example lactose, talc, silica, aluminum hydroxide, calcium silicate and polyamide powders, or mixtures of these substances. Sprays can additionally contain the customary propellants, for example chlorofluorohydrocarbons.

Solutions and emulsions can contain the customary excipients in addition to the active compound or compounds, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, olive oil castor oil and sesame oil, glycerol, glycerol-formal, tetrahydrofurfuryl alcohol, polyethylene glycols and fatty acid esters of sorbitan, or mixtures of these substances.

For parenteral administration, the solutions or emulsions can also be in a sterile form, which is isotonic with blood.

Suspensions can contain the customary excipients in addition to the active compound or compounds, such as liquid diluents, for example water, ethyl alcohol or propylalcohol, suspending agents, for example ethoxylated isostearyl alcohols, polyoxyethylene sorbitol esters and sorbitan esters, microcrystalline cellulose, aluminum metahydroxide, bentonite, agar-agar and tragacanth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical preparations in a concentration of about 0.1 to 99.5, preferably 0.5 to 95, % by weight of the total mixture. The abovementioned pharmaceutical preparations can also contain other pharmaceutical active compounds in addition to the active compounds according to the invention.

The abovementioned pharmaceutical preparations are manufactured in the usual manner according to known methods, for example by mixing the active compound or compounds with the excipient or excipients.

The present invention also includes the use of the active compounds according to the invention, and of pharmaceutical preparations which contain one more active compounds according to the invention, in human and veterinary medicine for the prevention, amelioration and/or cure of the abovementioned illnesses.

The active compounds or the pharmaceutical preparations can be administered locally, orally, parenterally, intraperitoneally and/or rectally, preferably parenterally, especially intravenously.

In general, it has proved advantageous both in human medicine and in veterinary medicine to administer the active compound or compounds according to the invention in total amounts of about 2.5 to about 200, preferably 5 to 150, mg/kg of body weight every 24 hours, optionally in the form of several individual administrations, in order to achieve the desired results.

On oral administration, the active compounds according to the invention are administered in total amounts of about 2.5 to about 200, preferably 5 to 150, mg/kg of body weight every 24 hours, and on parenteral administration they are administered in total amounts of about 2.5 to about 50, preferably 1 to 25, mg/kg of body weight every 24 hours.

However, it can be necessary to deviate from the dosages mentioned, and in particular to do so as a function of the nature and body weight of the subject to be treated, the nature and the severity of the illness, the nature of the preparation and of the administration of the medicine, and the time or interval over which the administration takes place. Thus, it can suffice in some cases to manage with less than the abovementioned amount of active compound, while in other cases, the abovementioned amount of active compound must be exceeded. The particular required optimum dosage and the type of administration of the active compounds can easily be decided by anyone skilled in the art on the basis of his expert knowledge.

PREPARATION EXAMPLES:

EXAMPLE 1

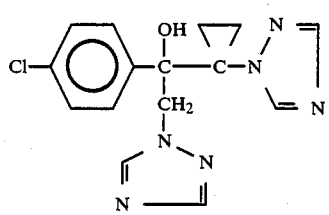
(I-1)

(Process a) 1st step

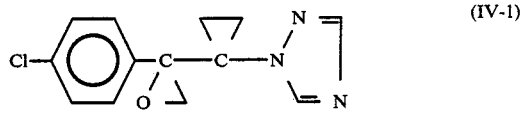
(IV-1)

100 ml of dry dimethyl sulphoxide are added dropwise to a mixture of 3.7 g of sodium hydride (80% pure) and 26.1 g of trimethylsulphoxonium iodide at 10° C., and the mixture is allowed to stir at room temperature for 1 hour. Then, 24 g of 1-(4-chlorobenzoyl)-1-(1,2,4-triazol-1-yl)cyclopropane in 50 ml of dimethyl sulphoxide are added dropwise. The reaction mixture is stirred at room temperature for two days. It is then poured onto 600 ml of ice-water, and the mixture is extracted several times with ethyl acetate, and the combined organic phases are washed with water, dried over sodium sulphate and evaporated in vacuo. 27.2 g of crude 1-[1-(4-chlorophenyl)oxiranyl]-1-(1,2,4-triazol-1-yl)cyclopropane are obtained as a yellowish oil which is immediately reacted further. Refractive index $n_D^{20}$: 1.5635.

2nd step

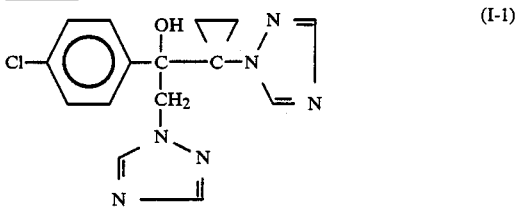
(I-1)

18 g of crude 1-[1-(4-chlorophenyl)oxiranyl]-1-(1,2,4-triazol-1-yl)cyclopropane (Example IV-1), 9.5 g of potassium carbonate and 15 g of 1,2,4-triazole in 100 ml of acetonitrile are heated under reflux for 8 hours. The reaction mixture is then evaporated in vacuo, and the residue is taken up in a mixture of water and methylene chloride. The organic phase is separated off, washed with water, dried over sodium sulphate and evaporated in vacuo. The residue is stirred with toluene, filtered off with suction and recrystallized from 300 ml of ethanol. 10 g (44% of theory) of 1-(4-chlorophenyl)-1-[1-(1,2,4-triazol-1-yl)cyclopropyl]-2-(1,2,4-triazol-1-yl)-1-ethanol, of melting point 211° C. are obtained.

PREPARATION OF THE STARTING MATERIAL

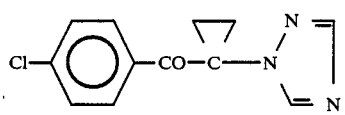
(II-1)

A solution of 150 g of 4-chlorophenyl 1-bromo-3-chloropropyl ketone in 200 ml of acetone is added dropwise to a boiling solution of 100 g of potassium carbonate and 110 g of 1,2,4-triazole in 400 ml of acetone, and the mixture is then stirred under reflux for 8 hours. It is then evaporated in vacuo, and the residue is stirred in 500 ml of water. The precipitate which separates out is filtered off with suction, washed several times with water and dried. 104 g (82% of theory) of 1-(4-chlorobenzoyl)-1-(1,2,4-triazol-1-yl)cyclopropane, of melting point 78° C., are obtained.

(PROCESS B)

A solution of 15.1 g of 1-(4-chlorophenyl)-2,3-di(1,2,4-triazol-1-yl)-1-propanone in 75 ml of dimethyl sulphoxide is added dropwise to a mixture of 24.2 g of trimethylsulphoxonium iodide and 12.3 g of potassium tert.-butylate in 60 ml of dimethyl sulphoxide. The reaction mixture is stirred at room temperature for 18 hours. It is then evaporated in vacuo; the residue is dissolved in methylene chloride, and the solution is washed with water, dried over sodium sulphate and evaporated. The residue is purified by chromatogrpahy (silica gel/-methylene chloride). The residual oil is induced to crystallize by stirring with ether. 6.3 g (38.2% of theory) of 1-(4-chlorophenyl)-1-[1-(1,2,4-triazol-1-yl)cyclopropyl]-2-(1,2,4-triazol-1-yl)-1-ethanol of melting point 208° C., are obtained.

PREPARATION OF THE STARTING MATERIAL

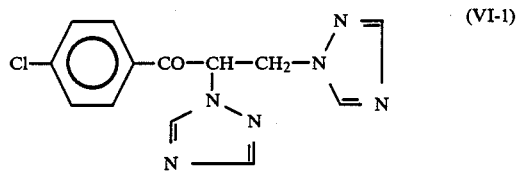
(VI-1)

A mixture of 44.3 g of 4-chlorophenyl 1,2,4-triazol-1-ylmethyl ketone, 19.6 g of 1-hydroxymethyl-1,2,4-triazole, 300 ml of toluene, 6 g of acetic acid and 2 ml of piperidine is heated under a water separator until separation of water is complete. The mixture is allowed to cool, and the resulting crystalline precipitate is filtered off with suction and washed with diisopropyl ether. 47 g (76% of theory) of 1-(4-chlorophenyl)-2,3-di(1,2,4-triazol-1-yl)-1-propanone of melting point 204° C., are obtained.

In an analogous manner and in accordance with the process according to the invention, it is possible to obtain the compounds of the formula (I)

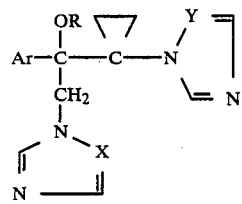
(I)

which are listed in Table 1 which follows:

| Example No. | Ar | R | X | Y | Melting point (°C.) |
|---|---|---|---|---|---|
| I-2 | F—⌬— | H | N | N | 182 |
| I-3 | ⌬—⌬— | H | N | N | 184 |
| I-4 | (CH₃)₂CH—⌬— | H | N | N | 167 |
| I-5 | CH₃—⌬— | H | N | N | 148 |
| I-6 | ⌬— | H | N | N | 146 |
| I-7 | Br—⌬— | H | N | N | 202 |
| I-8 | Cl,Cl—⌬— | H | N | N | 166 |
| I-9 | CH₃O—⌬— | H | N | N | 178 |
| I-10 | Cl—⌬— | H | N | CH | 196 |
| I-11 | CH₃O—⌬— | H | H | N | 213 |

In accordance with Example 1 and in accordance with the process conditions indicated, it is possible to obtain the precursors of the formula (II)

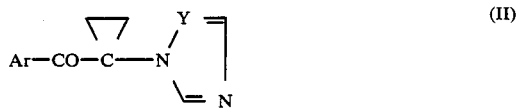
(II)

which are listed in Table 2 which follows:

| Example No. | Ar | Y | Melting point (°C.) |
|---|---|---|---|
| II-2 | F—⌬— | N | 69 |
| II-3 | ⌬—⌬— | N | 169 |

-continued

| Example No. | Ar | Y | Melting point (°C.) |
|---|---|---|---|
| II-4 | 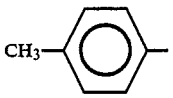 4-CH₃-C₆H₄ | N | 107 |
| II-5 | 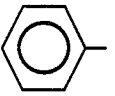 C₆H₅ | N | 78–81 |
| II-6 | 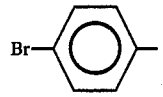 4-Br-C₆H₄ | N | 82 |
| II-7 | 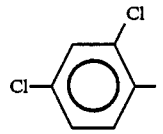 3,4-Cl₂-C₆H₃ | N | 84 |
| II-8 | 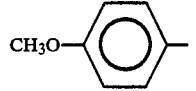 4-CH₃O-C₆H₄ | N | 90 |
| II-9 | 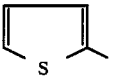 2-methylthiophene | N | 91 |

In accordance with Example 1 and in accordance with the process conditions indicated, it is possible to obtain the intermediates of the formula (IV)

(IV)

which are listed in *Table 3* which follows:

| Example No. | Ar | Y | Physical constant |
|---|---|---|---|
| IV-2 |  4-F-C₆H₄ | N | $n_D^{20}$: 1.5412 |
| IV-3 |  biphenyl | N | oil |
| IV-4 | 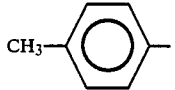 4-CH₃-C₆H₄ | N | oil |
| IV-5 | 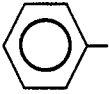 C₆H₅ | N | oil |
| IV-6 | 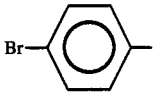 4-Br-C₆H₄ | N | oil |
| IV-7 | 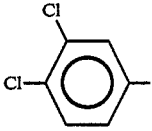 3,4-Cl₂-C₆H₃ | N | oil |
| IV-8 | 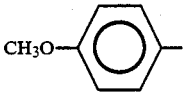 4-CH₃O-C₆H₄ | N | oil |

In accordance with Example 1 and in accordance with the process conditions indicated, it is possible to obtain the precursors of the formula (VI)

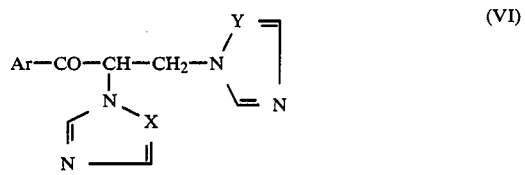

(VI)

which are listed in *Table 4* which follows:

| Example No. | Ar | X | Y | Melting point (°C.) |
|---|---|---|---|---|
| VI-2 |  4-F-C₆H₄ | N | N | 185 |
| VI-3 | 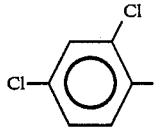 3,4-Cl₂-C₆H₃ | N | N | $n_D^{20} = 1.5504$ |
| VI-4 |  biphenyl | N | N | 195 |
| VI-5 | 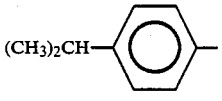 4-(CH₃)₂CH-C₆H₄ | N | N | 170 |
| VI-6 | 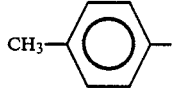 4-CH₃-C₆H₄ | N | N | 212 |
| VI-7 | 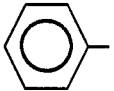 C₆H₅ | N | N | 170 |

USE EXAMPLES

The compounds which are indicated below and which are disclosed in EP-OS (European Published Specification) 0,044,605 are used as comparison substances in the in vitro test:

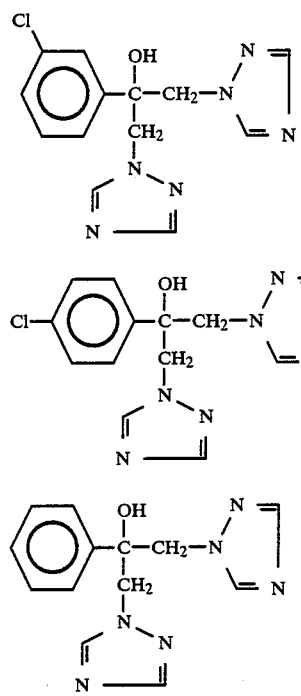

EXAMPLE A

IN VITRO ANTIMYCOTIC ACTIVITY

Description of the test

The in vitro tests were carried out in a serial dilution test using inocula of organisms with an average of $5 \times 10^3$ to $10^4$ organisms/ml of substrate. The following nutrient medium were used (a) for dermatophytes and mold fungi: Sabourand's milieu d'epreuve (b) for yeasts: meat extract/glucose broth.

The incubation temperature was 28° to 37° C., and the incubation time was 24 to 96 hours for yeasts and 96 hours for dermatophytes and mold fungi.

In this test, for example the compounds 1, 3, 6 and 7 according to the invention showed a better antimycotic action than compounds (A), (B) and (C) known from the state of the art.

TABLE A

| Active compound | In vitro antimycotic activity MIC values in mcg/ml of nutrient medium | | | | |
|---|---|---|---|---|---|
| | Trichophyton mentagr. | Microsporum canis | Candida albicans | Torulopsis glabrata | Aspergillus fumigatus |
| (A) (known) | 32 | — | >264 | >64 | >64 |
| (B) (known) | 16 | — | 2 | 64 | >64 |
| (C) (known) | 64 | — | 64 | >64 | >64 |
| Compounds according to Preparation Example: | | | | | |
| I-1 | 2 | 32 | 8 | >64 | 32 |
| I-3 | <1 | 4 | 2 | 8 | 8 |
| I-6 | 4 | 32 | 8 | >64 | 32 |

TABLE A-continued

| Active compound | In vitro antimycotic activity MIC values in mcg/ml of nutrient medium | | | | |
|---|---|---|---|---|---|
| | Trichophyton mentagr. | Microsporum canis | Candida albicans | Torulopsis glabrata | Aspergillus fumigatus |
| I-7 | <1 | 32 | 4 | 32 | 64 |

EXAMPLE B

IN VIVO ANTIMYCOTIC ACTIVITY (ORAL) ON CANDIDOSIS OF THE MOUSE

Description of the Test

Type SPF-CF$_1$ mice were infected intravenously with $1-2 \times 10^6$ logarithmically growing candida cells which are suspended in physiological saline solution. The animals are each treated orally with 10–100 mg/kg of body weight of the products 1 hour before and 7 hours after the infection.

Result

Untreated animals died on days 3 to 6 after the infection. The survival rate on day 6 after the infection was about 5% for untreated control animals.

In this test, for example the compounds 1, 2, 3, 5, 6, 7 and 10 according to the invention showed good or very good actions, that is to say >60% surviving on day 6 after infection.

TABLE B

| In vivo antimycotic action (oral) on candidosis of the mouse | |
|---|---|
| Active compound | Action |
| I-1 | +++++ |
| I-2 | +++++ |
| I-3 | +++ |
| I-5 | ++++ |
| I-6 | +++++ |
| I-7 | ++++ |
| I-10 | +++ |

Explanation of symbols:
+++++ = very good action = 90% surviving on day 6 after infection
++++ = good action = 80% surviving on day 6 after infection
+++ = action = 60% surviving on day 6 after infection
++ = weak action = Less than 40% surviving on day 6 after infection
k.W. = no difference from the untreated infection control.

It is understood that the specification and examples are illustrative but not limitative of the present invention and that other embodiments within the spirit and scope of the invention will suggest themselves to those skilled in the art.

We claim:

1. A method of combating mycoses which comprises administering to a patient in need thereof an antimycotic effective amount of an azolylcyclopropyl-azolylmethyl-carbinol derivative of the formula

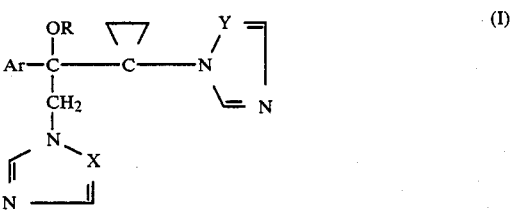

(I)

in which

Ar is phenyl which optionally carries at least one substituent selected from the group consisting of halogen, alkyl, alkoxy and alkylthio each having 1 to 4 carbon atoms; halogenoalkyl, halogenoalkoxy and halogenoalkylthio each having 1 to 2 carbon atoms and 1 to 5 identical or different halogen atoms; phenyl or phenoxy each of which is optionally substituted by alkyl having 1 or 2 carbon atoms and/or halogen; or represents naphthyl and a 5- to 6-membered heteroaromatic which optionally carries at least one substituent and nitrogen, oxygen and/or sulphur as the heteroatoms, the substituents being the abovementioned phenyl substituents, R is hydrogen, alkyl having 1 to 4 carbon atoms, alkenyl and alkinyl each having 2 to 4 carbon atoms, trialkylsilyl having 1 to 4 carbon atoms in each alkyl moiety, alkylcarbonyl having 1 to 4 carbon atoms in the alkyl moiety, or is phenylalkyl which optionally carries at least one substituent, with 1 to 2 carbon atoms in the alkyl moiety, the substituents being the phenyl substituents already mentioned for Ar, X is a nitrogen atom or the CH group, and Y is a nitrogen atom or the CH group, or an acid addition salt thereof.

2. A method according to claim 1, in which

Ar is phenyl which optionally has one to three substituents selected from the group consisting of fluorine, chlorine, methyl, isopropyl, tert.-butyl, methoxy, methylthio, trifluoromethyl, trifluoromethoxy, trifluoromethylthio, and phenyl or phenoxy each of which is optionally substituted by fluorine, chlorine and/or methyl; or is naphthyl, or is furyl, thienyl, pyridinyl or pyrimidinyl, each of which optionally has one or two substituents selected from the abovementioned phenyl substituents; and $R^1$ is hydrogen, methyl, ethyl, n-propyl, isopropyl, n-butyl, isobutyl, allyl, propargyl, trimethylsilyl, methylcarbonyl, ethylcarbonyl, n-propylcarbonyl, isopropylcarbonyl, n-butylcarbonyl, isobutylcarbonyl, or is benzyl which optionally has one to three substituents selected from the phenyl substituents already mentioned for Ar.

3. A method according to claim 1, wherein the carbinol derivative is 1-(4-chlorophenyl)-1-[1-(1,2,4-triazol-1-yl)-cyclopropyl]-2-(1,2,4-triazol-1-yl)-1-ethanol.

4. A method according to claim 1, wherein the carbinol derivative is 1-(4-phenylphenyl)-1-[1-(1,2,4-triazol-1-yl)-cyclopropyl]-2-(1,2,4-triazol-1-yl)-1-ethanol.

* * * * *